United States Patent [19]

Bernstein et al.

[11] Patent Number: 5,679,377
[45] Date of Patent: Oct. 21, 1997

[54] PROTEIN MICROSPHERES AND METHODS OF USING THEM

[75] Inventors: Howard Bernstein, Cambridge; Eric Morrel, Needham; Edith Mathiowitz, Brookline; Kirsten Schwaller, Duxbury; Thomas R. Beck, Concord, all of Mass.

[73] Assignee: Alkermes Controlled Therapeutics, Inc., Cambridge, Mass.

[21] Appl. No.: 261,690

[22] Filed: Jun. 17, 1994

Related U.S. Application Data

[63] Continuation of Ser. No. 993,917, Dec. 18, 1992, abandoned, which is a continuation of Ser. No. 557,620, Jul. 24, 1990, abandoned, which is a continuation-in-part of Ser. No. 432,789, Nov. 6, 1989, abandoned.

[51] Int. Cl.$^6$ .............................. A61K 9/52; B01J 13/12
[52] U.S. Cl. .................. 424/491; 264/4.32; 264/4.6; 424/484; 424/485; 424/486; 427/2.14; 427/2.21; 427/213.31; 428/402.2; 428/402.21; 428/402.24; 514/866; 514/963; 514/965
[58] Field of Search ............................ 428/402.2, 402.21, 428/402.24; 424/460, 485, 486, 491, 484; 514/866, 963, 965; 427/2.14, 2.21, 213.31; 264/4.32

[56] References Cited

U.S. PATENT DOCUMENTS

| | | | |
|---|---|---|---|
| 2,481,412 | 9/1949 | Grindrod | 428/402.24 X |
| 3,092,553 | 6/1963 | Fisher, Jr. et al. | 428/402.2 X |
| 3,116,206 | 12/1963 | Brynko et al. | 428/402.2 X |
| 3,639,259 | 2/1972 | Scarpelli | 428/402.2 X |
| 3,880,991 | 4/1975 | Yolles | 424/432 |
| 3,937,668 | 2/1976 | Zolle | 264/4.3 |
| 3,939,259 | 2/1976 | Pescetti | 424/460 |
| 3,943,063 | 3/1976 | Morishita et al. | 427/213.36 |
| 4,069,307 | 1/1978 | Higuchi et al. | 424/432 |
| 4,107,288 | 8/1978 | Oppenheim et al. | 424/499 |
| 4,194,013 | 3/1980 | Rehacek et al. | 428/402.24 X |
| 4,332,790 | 6/1982 | Sozzi et al. | 424/498 |
| 4,349,530 | 9/1982 | Royer | 424/460 X |
| 4,359,483 | 11/1982 | Kaetsu et al. | 427/2.21 |
| 4,384,975 | 5/1983 | Fong | 427/213.36 |
| 4,391,797 | 7/1983 | Folkman et al. | 424/425 |
| 4,420,442 | 12/1983 | Sands | 264/13 |
| 4,492,720 | 1/1985 | Mosier | 264/4.6 X |
| 4,619,913 | 10/1986 | Luck et al. | 424/484 X |
| 4,711,782 | 12/1987 | Okada et al. | 424/455 |
| 4,818,542 | 4/1989 | DeLuca et al. | 424/491 |
| 4,861,627 | 8/1989 | Mathiowitz et al. | 427/213.31 |
| 4,885,357 | 12/1989 | Larkins et al. | 530/373 |
| 4,940,588 | 7/1990 | Sparks et al. | 424/490 |
| 4,952,402 | 8/1990 | Sparks et al. | 424/419 |
| 5,021,248 | 6/1991 | Stark et al. | 426/96 |
| 5,023,080 | 6/1991 | Gupta | 424/484 X |
| 5,069,936 | 12/1991 | Yen | 424/491 X |
| 5,271,961 | 12/1993 | Mathiowitz et al. | 427/213.31 |

FOREIGN PATENT DOCUMENTS

| | | |
|---|---|---|
| 0 000 667 | 2/1979 | European Pat. Off. . |
| 0 077 956 | 5/1983 | European Pat. Off. . |
| 0 158 277 | 10/1985 | European Pat. Off. . |
| 0 266 119 | 5/1988 | European Pat. Off. . |
| 2 166 651 | 5/1986 | United Kingdom . |
| WO88/01213 | 2/1988 | WIPO . |
| WO89/08449 | 9/1989 | WIPO . |
| WO90/03123 | 4/1990 | WIPO . |

OTHER PUBLICATIONS

Couvreur, et al., *Polymeric Nanoparticles and Microspheres*, pp. 27–43 Guiot and Douvreur, Eds. (CRC Press, 1986).
Damge, et al., *Diabetes* 37, 246,251 (1988).
Eldridge, et al., *Current Topics in Microbiology and Immunology* 146, 59–65 (1989).
Oppenheim, Polymeric Nanoparticles and Microspheres, pp. 1–25, Guiot and Couvreur, Eds. (CRC Press 1986).
Rhine, W.D., et al., *Journal of Pharmaceutical Sciences* 69:3, 265–270 (1980).
Matsuda, et al., *Chem. Pharm. Bull.* 37,757–759 (1989).
Suzuki, et al., *Chem. Pharm. Bull.* 37(4), 1051–1054 (1989).
Sato, T., et al., *Pharmaceutical Research* 5:1, 21–30 (1988).

*Primary Examiner*—Richard D. Lovering
*Attorney, Agent, or Firm*—Hamilton, Brook, Smith & Reynolds, P.C.

[57] ABSTRACT

Biodegradable, protein microspheres for in vivo release of a biologically active agent, as well as agricultural and environmental applications. The microspheres can be administered orally, intravenously, or subcutaneously for subsequent release. By selecting particular size ranges and the specific protein used to form the microsphere, it is possible to target the microspheres to a cell types such as macrophages, or to effect localized absorption of the microspheres to regions such as the mucosal membranes of the mouth, gastrointestinal tract, or urogenital areas. Larger forms of the microspheres can also be made using standard techniques of the desirable degradation properties.

23 Claims, 2 Drawing Sheets

PROTEIN MICROSPHERES AND METHODS OF USING THEM

BACKGROUND OF THE INVENTION

This is a continuation of application Ser. No. 07/993,917 filed on Dec. 18, 1992 and now abandoned, which is a continuation of application Ser. No. 07/557,620 filed on Jul. 24, 1990, and now abandoned which, is a continuation-in-part of U.S. Ser. No. 07/432,789 entitled "Absorbable Prolamine Microparticles and Methods of Using Them" filed Nov. 6, 1989 by Howard Bernstein, Eric Morrel, Edith Mathiowitz and Kirsten Schwaller, now abandoned.

A number of processes have been utilized to make microspheres and microcapsules for a variety of applications. Most microspheres are made of synthetic polymers, such as poly(lactic acid) or polyorthoesters, and are formed by solvent evaporation, spray drying, or phase separation. When the microspheres or microcapsules are used for drug delivery, the process must yield a product that is small, consistent in size and drug distribution, and with controlled degradation properties. One example of the use of polymeric microcapsules or microspheres is described in PCT/US89/01083, published Sep. 21, 1989, which discloses the use of polymeric microspheres for oral immunization of animals.

Proteins have also been used to form microparticles or microspheres for drug delivery. R. C. Oppenheim, *Polymeric Nanoparticles and Microspheres* Guiot and Couvreur, editors, chapter 1, pp. 1–25 (CRC Press, 1986), reviews formation, properties and drug delivery using proteins. Most are crosslinked in solution using glutaraldehyde, or hardened at elevated temperatures. Unfortunately, there are problems with significant loss of biological activity of incorporated materials and lack of controlled size and in vivo degradation rates. For example, zein microspheres prepared as carriers for chemotherapeutic agents by crosslinking a zein solution containing the drug, as reported by Suzuki, et al., *Chem. Pharm. Bull.* 37(4), 1051–1054 (1989), were quite heterogeneous in size, and displayed incorporation of less than 30% of the drug. This same group reported in *Chem. Pharm. Bull.* 37, 757–759 (1989), that yield and size range were improved by addition of a catalytic amount of dl-camphorsulfonic acid and rapid addition of polyvinylpyrrolidone, a surfactant and binder. Incorporation of drug was still less than 35%, however. PCTUS87/02025 by Clinical Technologies Associates, Inc., reports the preparation and use for drug delivery of microspheres made of "protenoids", thermal condensation polymers of mixed amino acids. While these materials have useful properties, they are designed for specific applications and targeted release as a function of pH.

In a similar process, proteins have been used to make glutaraldehyde crosslinked beads incorporating bacteria for agricultural applications.

Proteins have also been used to make implants for drug delivery, as well as coatings and plasticizers for drug-containing polymeric microcapsules. For example, EPO 158277 to Hoechst AG describes an implantable preparation for the controlled release of a peptide, buserelin, using zein as the carrier, formed by dissolving the peptide and the zein in alcohol, spray drying and shaping the resulting mixture. EPO 077956 to Tanabe Seiyaku Ltd. describes the use of zein and other proteins as enteric coatings for microcapsules, formed using standard techniques for coating, i.e., spray coating or dipping.

None of these methods of producing protein drug delivery devices can be used to incorporate high percentages of biologically active substances, especially labile substances, into uniform microspheres small enough to pass directly into the bloodstream when delivered orally, or with consistent release rates and sizes. None of the other processes yield a material having no binder or crosslinking agent present, that consists only of the natural protein. Moreover, while the above systems are useful for many applications, they are not appropriate for some applications, such as delivering orally administered drugs directly into the bloodstream. Oral administration of drugs is often the most desirable and convenient method. A need exists for systems that can successfully deliver these agents which have favorable release kinetics and allow the drug to be distributed or targeted in the host.

It is therefore an object of the present invention to provide methods for using biodegradable protein microspheres, for controlled or targeted drug delivery, systemically or topically, especially for delivery of labile substances and hydrophobic compounds.

It is another object of the present invention to provide a method for controlled, delayed release of agents into the environment, including enzymes, pesticides, and fertilizers.

It is a further object of the present invention to provide a method for directed delivery of compounds to mucosal membranes and the lining of the gastrointestinal tract.

It is still another object of the present invention to provide biodegradable, non-toxic diagnostic agents for use in methods such as radioimaging.

SUMMARY OF THE INVENTION

Biodegradable protein microspheres are used for in vivo release of a biologically active agent, as well as agricultural and environmental applications. A variety of materials can be incorporated into the microspheres, including biologically active agents such as proteins, organic compounds, metals, salts, chelating agents, and radioimaging/radiopaque agents. The microspheres can be administered enterally, topically (to the skin, eyes, or orifices), parenterally, or subcutaneously for subsequent release. By selecting particular size ranges and the specific protein used to form the microsphere, it is possible to target the microspheres to a cell types such as macrophages, or to effect localized absorption of the microspheres to regions such as the mucosal membranes of the mouth, gastrointestinal tract, or urogenital areas. Larger aggregate forms of the microspheres can also be made using standard techniques to compress and bind the microspheres without loss of the desirable properties, or by encapsulating the microspheres in a polymeric matrix.

DETAILED DESCRIPTION OF THE INVENTION

Figure 1A:
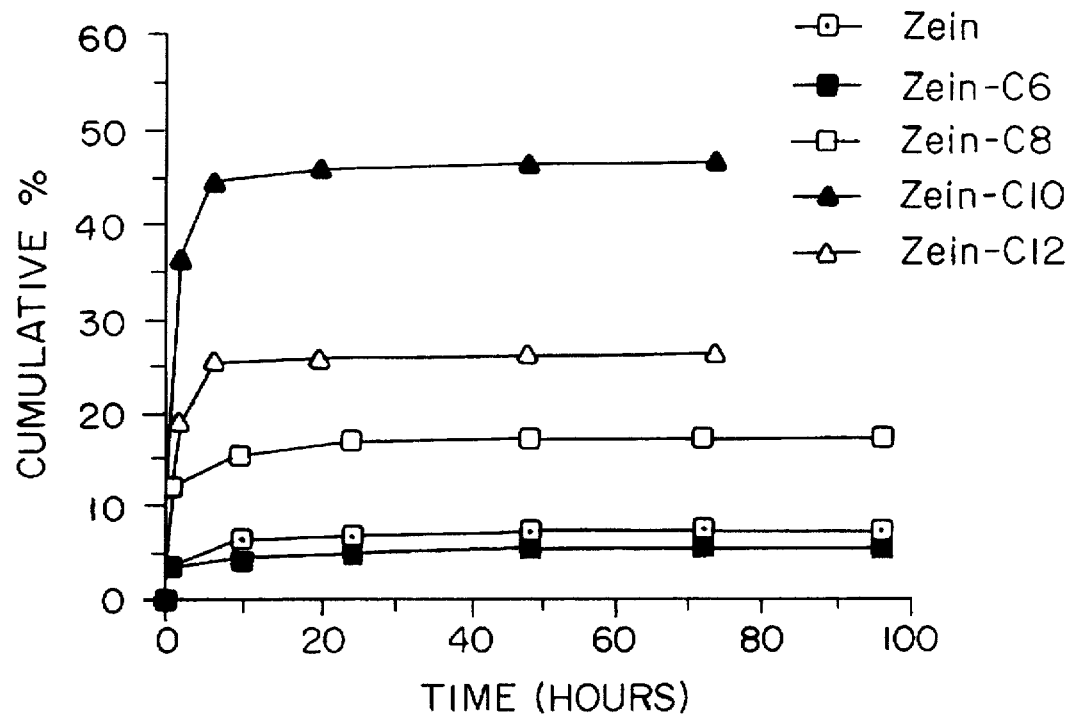
FIG. 1A is a plot of the % cumulative release of insulin into PBS from insulin containing microspheres prepared from zein and zein modified with hexanoic anhydride (C6), octanoic anhydride (C8), decanoic anhydride (C10) and lauric anhydride (C12) all having a 17% (w/w) loading of insulin versus time in hours.

A method of delivery of a biologically active agent in which protein microspheres containing the agent are administered to a human or animal, or placed at a site for release of the agent by diffusion from and/or degradation of, the microspheres. The protein microspheres have several advantages. The protein matrix is a natural, biodegradable substance, which metabolizes in the body to peptides and/or amino acids. The proteins can be modified, chemically or enzymatically, to endow them with desirable properties, such as a selected degradation rate. The process for making the microspheres from a protein solution does not require high temperature heating or cross-linking which could degrade material to be incorporated. Moreover, when used for drug delivery, the microspheres can be designed to be absorbed through the intestinal epithelium into the bloodstream and/or lymphatic system, or targeted to specific organs or phagocytic cells. The microspheres thereby have at least three distinct advantages for controlled delivery: protection of agents which would be attacked and/or degraded by the harsh conditions of the alimentary tract or enzymes in the blood; targeting of a site for release (such as phagocytic cells, mucosal membranes, or the blood, and controlled time and rate of release of agent.

I. Agents for incorporation into the microspheres.

A variety of different agents can be incorporated into the microspheres. Compounds can be incorporated in (1) the protein matrix forming the microspheres, (2) microparticle(s) surrounded by the protein which forms the microspheres, (3) a polymer core within the protein microsphere, (4) a polymer coating around the protein microsphere, (5) mixed in with microspheres aggregated into a larger form, or a combination thereof.

Both hydrophobic and hydrophilic compounds can be incorporated into the microspheres. Hydrophobic compounds can usually be co-solubilized in the aqueous/organic phase solution with the protein. Hydrophilic compounds are usually dispersed in the protein solution as particulates, although the double emulsion process or binary solvent systems described below can be used to solubilize the compounds. The use of particulates results in a higher burst of compound being released initially, as compared to when the compound is solubilized in the protein solution.

For drug delivery, biologically active agents having therapeutic, prophylactic or diagnostic activities can be delivered. These can be organic or inorganic compounds, proteins, or a wide variety of other compounds, including nutritional agents such as vitamins, minerals, amino acids and fats. Examples of agents include hormones, antigens, antibiotics, steroids, decongestants, neuroactive agents, and anesthetics or sedatives. The agents can be in various forms, such as uncharged molecules, components of molecular complexes, or pharmacologically acceptable salts, such as hydrochloride, hydrobromide, sulfate, phosphate, nitrate, borate, acetate, maleate, tartrate and salicylate. For acidic drugs, salts of metals, amines or organic cations (e.g., quaternary ammonium) can be used. Simple derivatives of the drugs (such as ethers, esters, and amides), which have desirable retention and release characteristics, can also be used.

Imaging agents including metals, radioactive isotopes, radiopaque agents, and radiolucent agents, including air, can also be incorporated. Air can be encapsulated by sonicating or agitating the protein solution before making the microspheres. Radioisotopes and radiopaque agents include gallium, technetium, indium, strontium, iodine, barium, and phosphorus.

Various other non-biologically active agents such as colors, flavorings and fragrances can also be incorporated, alone or in combination with the biologically active agents.

Other compounds that can be incorporated include pesticides, fertilizers, pheremones, and agents used in environmental cleanup (including bacteria, chelating agents, and enzymes such as lipases and proteases).

The amount of compound incorporated in the delivery device varies widely depending on the particular agent, the desired effect and the time span over which it takes the matrix to release the compound. The upper and lower limits on the amount of the compound to be incorporated into the device can be determined empirically by comparing microspheres containing a range of compound.

In the embodiment wherein a compound to be released is incorporated into a microsphere surrounded by a coating, a second compound can be incorporated into the coating, such that the second compound is released initially from the coating, followed by release of the first compound by diffusion from or degradation of the microsphere. This may be particularly advantageous for delivery of an antigen, where antigen is incorporated into the coating and the microsphere and degradation rates are designed to release antigen at distinct intervals, thereby maximizing the immunogenic response.

II. The Microspheres, method of making and characterization.

As used herein, "micro" refers to a particle having a diameter of from nanometers to micrometers. Microspheres are solid spherical particles; microparticles are particles of irregular or non-spherical shape. A microsphere may have an outer coating of a different composition than the material originally used to form the microsphere. Unless otherwise noted, the term microspheres can be used to encompass microcapsules and the term microparticles can be used to encompass microparticles, microspheres, and microcapsules. A "composite microsphere" is a microsphere formed of at least two different materials, either a protein and a polymer or two proteins. A "composite" is an aggregation of microspheres made as described herein, bound by materials known to those skilled in the art for this purpose.

Using the method described herein, protein microspheres are prepared by a phase separation, solvent removal process. The formation of the microspheres depends upon the differential solubility of proteins in water-miscible organic solvents, salt solutions, or acidic or basic solutions, as compared to their solubility in an immiscible phase, such as a nonpolar organic solvent or an oil. Most proteins are not soluble in oils. Accordingly, protein is dissolved in a first solvent which is a water-miscible organic, organic/aqueous, or binary organic solvent, acid, base or salt solution (the encapsulating phase). The compound to be incorporated, in the form of a suspension, emulsion, solution or particles, is added to the protein solution. This mixture is then contacted with a second liquid phase (the continuous phase) which does not dissolve the proteins and has limited miscibility with the first solvent. The continuous phase is preferably an oil, such as vegetable oil, silicone oil or mineral oil. Vigorous agitation is applied, and the first solvent is removed under conditions sufficient to form microspheres, usually by evaporation or extraction.

Coatings can also be made onto microparticles made of protein or non-protein polymers. To make the coatings, (1)

protein is first dissolved in a solvent; (2) the particles or microparticles to be coated are added to the solution; (3) the protein/microparticle mixture is added to a second liquid phase which is immiscible with the first solvent and a non-solvent for the protein coating; (4) the mixture is agitated; and (5) the first solvent is removed (usually by evaporation or extraction) under conditions sufficient to cause the particles or microparticles to be coated with a protein coating.

The process described herein yields protein microspheres having a diameter of between nanometers and micrometers, with an average diameter between 0.01 micron to less than about 100 microns, having incorporated therein a compound to be delivered or released at a desired time and/or site. In the preferred method, the microspheres are stored frozen to enhance the stability of incorporated compounds over extended periods of time.

Composites containing the protein microspheres can be formed using standard techniques to encapsulate the protein microspheres in a polymer, either degradable or non-degradable, natural or synthetic. These materials are known to those skilled in the art. The protein microspheres can also be compressed or shaped by other techniques known to those skilled in the art.

Proteins useful for forming the microspheres.

In the preferred embodiments, the proteins are hydrophobic proteins such as prolamines, preferably zein. As used herein, proteins can be a single type of protein, a combination of proteins, or a combination of protein with polymer. Proteins are used to make the microspheres since they are natural, offer a diversity of properties and are degraded in vivo into innocuous amino acids or small peptides. Hydrophobic proteins have limited solubility in water and are soluble in organic solvents, aqueous mixtures of organic solvents, and binary mixtures of organic solvents. Examples of other useful proteins besides prolamines are collagen, casein, and keratin.

Prolamines are characterized by having a large number of hydrophobic amino acids, such as glutamine, asparagine and proline. Prolamines are water-insoluble, but are soluble in many organic solvents, particularly alcohols, containing at least one percent (1%) water, but no more than sixty percent water, or a polar organic solvent.

Prolamines are readily available and inexpensive, for example, as the by-products of grain processing. Representative prolamines include gliadin, kafirin, zein and hordein. A preferred prolamine for use in making microspheres is zein. Both commercially available grades and purified forms of zein can be used. The properties of zein are described in detail by L. C. Swallen in: "Zein—A New Industrial Protein", *Ind. and Eng. Chem.*, 33:394–398 (1941).

Solvents for the proteins used to form the microspheres.

The protein is dissolved in an appropriate solvent. The protein is "soluble" if more than 0.5% (w/v) of the protein dissolves in the solvent to form a visually transparent solution at room temperature (about 20°–25° C.). Prolamines are soluble, for example, in alcohols (ethanol), some ketones (e.g., methyl ethyl ketone, acetone) and amide solvents (e.g., acetamide), containing between 5% and 60% water; in extremely high (e.g., pH 10 or greater) or extremely low (pH 2 or less) pH solutions; and in aqueous solutions of from about 1.0 to about 6N inorganic salts (e.g., NaCl, KBr).

Many binary solvent systems for zein are known, in which the primary components are polyols, especially lower aliphatic alcohols, ketones, or glycols, and the secondary components are water, aromatic hydrocarbons, halogenated hydrocarbons, especially chlorinated hydrocarbons, nitroparaffins, aldehydes and cyclic ethers. Specific examples include mixtures of alcohols and halogenated hydrocarbons and mixtures of alcohols and propylene glycol with ethylene glycol. Binary solvent systems for prolamines such as zein are reported by Manley and Evans, *Industrial and Engineering Chemistry* 36, 661–665 (1943).

Suitable materials for the Continuous Phase.

The compound to be incorporated is added to the protein solution. The compound can be in the form of a suspension, solution (in oil, organic solvent or water), emulsion, or particles. The compound/protein mixture is then introduced into a second liquid phase, the continuous phase, which (1) is immiscible or of limited miscibility with the protein solvent and (2) does not dissolve the protein. Solvents are "immiscible" if they will not mix with each other to form a stable homogeneous solution at the operating temperature without mixing. Immiscible phases tend to form separate layers under these conditions. Oils such as mineral oil, silicone oil, or vegetable oil are useful immiscible phases. Others include hexane, heptane, dodecane, and high boiling point petroleum ether.

One or more surfactants can be added to the protein/first solvent mixture or to the continuous phase to reduce the size of the protein microspheres. Suitable surfactants, and methods of use thereof, are known to those skilled in the art.

Process for forming the Microspheres.

The protein solution was added to the continuous phase, and the first solvent removed, for example, preferably by evaporation, or by solvent extraction, under conditions forming microspheres. Efficient mixing can be achieved by fast mechanical stirring using a homogenizer and/or by using a baffled reactor to prevent laminar flow. If necessary, the mixture can be heated to a temperature of from between 22° C. and about 45° C. for a period of between about 15 minutes to 45 minutes. If heated, the mixture is first cooled to room temperature, then the microspheres incorporating the compound are washed, separated from the mixture, and dried. If the hydrophilic drug incorporated is unstable in aqueous media, the microspheres can be lyophilized.

In an alternative embodiment used when hydrophilic compounds are to be incorporated into the microspheres other than as particulates, a double emulsion technique is employed. For example, the compound to be incorporated is first dissolved in an aqueous solution. The zein is dissolved in a suitable binary organic mixture with low aqueous miscibility. Many binary organic solvents for zein are known, for example, mixtures of an alcohol, such as methanol, ethanol or isopropanol, with a halogenated hydrocarbon, with the halogenated hydrocarbon as the primary component. The aqueous solution is added to the organic solution of zein and a water in oil emulsion is created. This emulsion is then added to a second organic liquid phase, the continuous phase, which is immiscible or of limited miscibility with the organic solvent for zein, such as an oil, to form a double water in oil emulsion. This solvent is then removed, as described previously, to form microspheres.

Modification of the microspheres.

The properties of the microspheres can be modified for a given application, for example, by chemically and/or enzymatically altering the starting protein prior to forming the microspheres. Such modifications can produce a protein having enhanced or altered thermal stability, surface reactivity, lipophilicity, molecular weight, charge, shear stability and resistance to proteases.

Enzymatic modification of the protein.

The functionality, surface properties and molecular weight distribution of the protein can be modified by enzymatic treatment. For example, enzymatic hydrolysis of zein, having a dimer molecular weight of about 38,000 daltons, in 90% ethanol using a protease, such as papain or chymotrypsin, yields polypeptides with a molecular weight of about 1,000 daltons which retain the solubility characteristics of the intact protein, i.e., the polypeptides are still insoluble in water but soluble in 90% ethanol. The degree of hydrolysis can be controlled by varying the amount of enzyme used or the reaction time during which the protein is exposed to the enzyme.

The stability of the protein can be enhanced by crosslinking the protein prior to use in the phase separation process by the addition of an enzyme which catalyzes intra- and/or intermolecular crosslinking of the protein, such as transglutaminase, or protein disulfide isomerase. Transglutaminase and protein disulfide isomerase cause inter- and intramolecular crosslinking of the protein through the amino acids glutamine and cysteine, respectively. Transglutaminase catalyzes an acyl transfer reaction, in which the amide group of the amino acid glutamine is the acyl donor. Other enzymatic processes are known which alter the properties of proteins, before or after formation of the microspheres.

Chemical modification of the protein.

The properties of the microspheres can also be altered by chemical modification of the proteins used in their preparation, either before or after formation of the microspheres. Such modifications can include treating the proteins with an acid, base or other agent which alters the structure of one or more amino acid side chains, which in turn alters the character of the protein. For example, the high glutamine and asparagine content of prolamines, particularly zein, provides a means for manipulating the charge characteristics of the protein, and therefore the hydrophobicity, by deamidation. The preferred deamidation method involves mild acid-catalyzed deamidation (at a pH of about 1) at elevated temperatures (between 25° C. and 65° C.) for a period of time sufficient to accomplish the desired level of deamidation. The deamidation process may be followed by measuring the release of ammonia with an ammonia electrode. Deamidation can be terminated by the addition of ammonium carbonate or other base.

Other examples of chemical modification include esterification of the protein with fatty alcohols, or acylation of the protein with fatty anhydrides, which can alter the acid (or base) sensitivity of the protein product. For example, zein or zein peptides can be deamidated as described above, then the deamidated zein reacted with a fatty acid to form the fatty acid ester of the protein. Non-deamidated or deamidated zein peptides can also be reacted with fatty alcohols to form fatty acylated zein or zein peptides. These fatty acid-modified proteins or peptides can then be used as starting material to form the microspheres.

The charge on the protein can also be modified by crosslinking amino acids or polyamino acids to the protein, using glutaraldehyde or carbodiimide.

Proteins can be modified before or after formation of the microspheres. However, an advantage of the phase separation process is that harsh chemical or heat treatment of the protein after formation of the microspheres is not required. Accordingly, when modification of the protein using agents such as glutaraldehyde for crosslinking of the protein is desirable, the protein is treated prior to incorporation of the compound to be delivered and formation of the microspheres.

Formation of protein-polymer microspheres.

Proteins can be combined with non-protein polymers to form composite microspheres. Bioerodible synthetic or natural polymers are preferred. The term "bioerodible", or "biodegradable", as used herein refers to materials which are enzymatically or chemically degraded in vivo into simpler chemical species. Polysaccharides are examples of natural polymers. Synthetic polymers which degrade in vivo into innocuous products include poly(lactic acid) (PLA), poly (glycolic acid) (PGA) and co-polymers of PLA and PGA, polyorthoesters, polyanhydrides, polyphosphazene, polycaprolactone, polyhydroxybutyrate, blends and copolymers thereof.

PLA, PGA and PLA/PGA copolymers are particularly useful for forming prolamine composite microspheres. PLA polymers are usually prepared from the cyclic esters of lactic acids. Both L(+) and D(−) forms of lactic acid can be used to prepare the PLA polymers, as well as the optically inactive DL-lactic acid mixture of mixtures of D(−) and L(+) lactic acids. Methods of preparing polylactides are well documented in the patent literature. The following U.S. Pat. Nos., the teachings of which are hereby incorporated by reference, describe in detail suitable polylactides, their properties and their preparation: 1,995,970 to Dorough; 2,703, 316 to Schneider; 2,758,987 to Salzberg; 2,951,828 to Zeile; 2,676,945 to Higgins; and 2,683,136; 3,531,561 to Trehu.

PGA is the homopolymer of glycolic acid (hydroxyacetic acid). In the conversion of glycolic acid to poly(glycolic acid), glycolic acid is initially reacted with itself to form the cyclic ester glycolide, which in the presence of heat and a catalyst is converted to a high molecular weight linear-chain polymer. PGA polymers and their properties are described in more detail in Cyanamid Research Develops World's First Synthetic Absorbable Suture", *Chemistry and Industry*, 905 (1970).

Both the release of the incorporated compound and the bioerosion of the matrix are related to the molecular weights of PLA, PGA or PLA/PGA. The higher molecular weights, weight average molecular weights of 90,000 or higher, result in polymer matrices which retain their structural integrity for longer periods of time; while lower molecular weights, weight average molecular weights of 30,000 or less, result in both slower release and shorter matrix lives.

Matrices made of either a protein mixture or a protein-polymer mixture, such as prolamine/PLA, prolamine/PGA or prolamine/PLA-PGA, can be designed with a variety of degradation and diffusion rates. In general, degradation is a function of the protein and polymer composition. Diffusion is a function of the matrix composition, form, and the nature of the incorporated material. Matrices can be synthesized to degrade over periods of time shorter than, equal to or longer than the period of release of incorporated compound. The compound can be released by diffusion, degradation of matrix, or a combination of diffusion through the matrix and release as the matrix degrades.

These composite matrices can take one of several forms: protein microspheres with a polymer coating; polymer microparticles or microcapsules encapsulated by protein; bioactive compounds and protein microspheres encapsulated by polymer; or protein microspheres with or without incorporated bioactive compound and bioactive compound encapsulated by polymer.

Sizes of microspheres produced by method.

The microspheres can be produced in a variety of sizes, ranging from nanometer-sized microspheres up to an average size of about 100 microns. Microspheres having an average particle size of from about 50 to 100 nm to about 20 microns are more preferred. Microspheres having an average particle size of from about 100 nm to about 5 microns are particularly preferred for use in drug delivery because microspheres in this size range may be absorbed into the bloodstream and/or lymphatic system or phagocytized.

The size and other characteristics of the microspheres can be determined using scanning electron microscopy, (SEM), light scattering and differential scanning calorimetry (DSC).

Preparation of protein coatings.

Protein coatings are made using a variation of the method to make microspheres. Particles (including particles of non-uniform shape, microspheres and microcapsules) to be coated can be made from any polymeric substance, usually non-protein substances or modified proteins, or material to be released. To form the coating, the protein is dissolved, the particles to be coated added to the protein solution, the protein/microparticle mixture added to the continuous phase, the mixture agitated and the solvent removed, preferably by evaporation, or by solvent extraction, under conditions causing the particles to be coated with a protein coating.

Preparation of Composites of the Microspheres.

The microspheres, either formed entirely of protein, protein in combination with polymer, or protein coated with protein, alone or in combination with bioactive agents, can be shaped into composites using techniques known to those skilled in the art. The preferred method is to compress the microspheres in a mold. Binders or surfactants can be added to facilitate formation of the composite. The microspheres can also be cast in a polymer solution which solidifies upon removal of the solvent or a decrease in temperature.

III. Methods for administration of compounds incorporated into protein microspheres or implants formed from microspheres.

The microspheres can be administered topically, locally or systemically by parenteral administration or enteral administration.

Enteral Administration.

Microspheres having biologically active agents are preferably administered orally. These microspheres, depending on the chemical nature and size, will either be absorbed to, or passed through, the epithelial lining of the gastrointestinal tract into the bloodstream or lymphatic system. The biologically active compound is released from the microspheres by diffusion, degradation, or a combination of degradation and diffusion, in the blood stream, lymphatic system, epithelium, or at the surface of the epithelium.

Parenteral Administration.

Microspheres of less than five microns readily pass through a needle for intravenous administration. Suitable pharmaceutical carriers, for example, a phosphate buffered saline, are known and commercially available. Intravenous administration may be preferred for targeted delivery of incorporated compounds to phagocytic cells, for example, of antiparasitic or anti-HIV drugs, where the pathogenic agent is also selective for these cell types.

Subcutaneous, Intramuscular and Intraperitoneal Administration.

Microspheres produced as described above are small enough to be injected through a standard gauge needle under the skin or into the peritoneum for subsequent release of incorporated drug. Adhesion of the microspheres to the peritoneum aids in localizing release of the incorporated drug. Microspheres can also be implanted or injected intramuscularly for immunization or other purposes where slower release into the bloodstream is desirable. Carriers such as phosphate buffer saline, or an adjuvant such as an oil, can be used as a carrier for the microspheres. Pharmaceutically acceptable carriers are known to those skilled in the art.

Topical Administration.

The microspheres can be administered topically to the skin, eyes, ears, nose, or any other orifice such as the rectum, mouth and urogenital tract. The prolamine microspheres adhere to mucosal membranes, aiding in targeted release to these areas. This can be advantageous in administration of drugs via the mouth, rectum, and vagina.

Microspheres are suspended in a suitable pharmaceutical carrier for administration using methods appropriate for the carrier and site of administration. For example, microspheres are administered to the eye in a buffered saline solution, approximately pH 7.4, or in an ointment such as mineral oil. The dosage will be dependent on the compound to be released as well as the rate of release. The microspheres, or aggregations of microspheres into films, disks, or tablets, with incorporated compound can be administered to the skin in an ointment or cream. Suitable pharmaceutical carriers are known to those skilled in the art and commercially available.

Sustained delivery of antibiotics or growth factors (amino acids, peptides, or protein growth factors) to open wounds is of particular therapeutic importance in a variety of medical and surgical situations including, but not limited to, thermal burns, chemical burns, surgical wounds, diabetic ulcers and vascular insufficiency.

Diagnostic Applications.

The microspheres containing radiopaque compounds, radioisotopes, or radiolucent compounds (including air) are particularly suited for use in diagnostic procedures. The microspheres can be administered parenterally or enterally. Microspheres that bind to mucosal membranes are particularly preferred for these applications, especially for imaging of the nasal and pharyngeal, gastrointestinal, and genitourinary tracts. Intravenous administration of microspheres containing imaging agents are particularly useful for imaging liver, spleen or lung.

Targeted Administration.

Delivery to mucosal membranes and regions of the mouth.

The microspheres formed of prolamines bind to oral, gastrointestinal and urogenital mucosal membranes. The microspheres also appear to bind to tooth enamel, which serves as a second site of attachment for directed delivery of the incorporated compounds in the pharyngeal area. There are many compounds for which this type of delayed release into the mouth would be advantageous, including antibiotics such as tetracycline, erythromycin, penicillins, cephalosporins, and metronidazole, antivirals, antihistamines, cardiovascular drugs such as nifedipine, nitroglycerine and ACE inhibitors, and oral hygiene products such as stannous fluoride and calcium chloride. This is of particular importance in the treatment of disorders such as periodontal disease, tooth caries, oral infections, and Candidiasis.

Although discussed with reference to microspheres, the aggregates of multiple microspheres can also be used for directed delivery to the mucosal membranes and tooth enamel. The larger forms are preferred for targeting delivery to gingiva, buccal mucosa, lingual mucosa, and dental surfaces.

Delivery to specific cells, especially phagocytic cells and organs.

Phagocytic cells within the Peyer's patches appear to selectively take up microspheres administered orally. Phagocytic cells of the reticuloendothelial system also take up microspheres when administered intravenously. Microspheres of less than five microns diameter can be injected without embolytic complications. Endocytosis of the microspheres by macrophages can be used to target the microspheres to the spleen, bone marrow, liver and lymph nodes.

The charge or lipophilicity of the microsphere is used to change the properties of the protein carrier. For example, the lipophilicity of prolamine microspheres can be modified by covalently linking fatty acids to the proteins, and the charge modified by covalently linking amino acids or polyamino acids to the proteins, by deamidating the protein or by addition of surfactants. Proteins can be crosslinked prior to forming the microspheres. Other modifications can be made before or after formation of the microsphere, as long as the modification after formation does not have a detrimental effect on the incorporated compound.

Targeting can also be enhanced or altered by selection of molecules binding to specific receptors on the targeted cells, where the binding molecules are attached to, or dispersed within, the protein forming the microspheres. Many cell types are characterized by specific surface receptors, ranging in specificity from just one type of cell or small group of individual patients to a broad class of cell types. For example, cells commonly infected by human immunodeficiency virus have a receptor for the virus called the CD4 receptor. Molecules, such as antibodies, binding to the CD4 receptor can be included as part of the outer surface of microspheres to specifically target the microspheres to the cells susceptible to HIV infection. Other cells have carbohydrate moieties which bind protein molecules called lectins. Incorporation of lectins into the microspheres can therefore be used to target the microspheres to cells having specific receptors for the lectins.

Release at a selected site in the environment.

The protein microspheres, or aggregations of microspheres, having compound incorporated therein, are useful in environmental applications to release active agent, particularly since they biodegrade into innocuous peptides and amino acids. The proteins forming the microspheres are selected for the desired release rate. Examples of materials to be incorporated for subsequent release include pesticides, fertilizers, chelating agents, and enzymes, including proteases, cellulases, lipases, and other enzymes such as those involved in degradation of plastics and polychlorinated biphenyls (PCBs).

The methods are further described with reference to specific embodiments demonstrating incorporation and release of biologically active insulin. Other proteins including catalase, hemoglobin, calcitonin and vasopressin have also been successfully incorporated and released.

EXAMPLE 1

Preparation of Prolamine microspheres containing particles of insulin, a protein.

Zein microspheres incorporating solid zinc insulin at two different loadings, 4.8% and 9% (w/w), were made. 0.4 g zein was dissolved in 8.0 ml of 90% ethanol (Pharmco Products, Inc., Norwalk, Conn.) to produce a 5% (w/v) zein (Type F-5000, Freeman Ind., Tuckahoe, N.Y.) solution. 0.02 g of insulin (Calbiochem, Inc., La Jolla, Caif.) was added to the 8.0 ml zein solution to produce microspheres with 4.8% loading. 0.04 g of insulin was added to 8.0 ml zein solution to produce microspheres with 9% loading. The insulin was added as particles since insulin is insoluble in ethanol. The insulin particles had a mean diameter of 3.2 microns.

The zein/alcohol/insulin mixture was introduced into 150 ml of cold corn oil (Mazola Corn Oil) and homogenized (Virtis Homogenizer, Virtis Corp.) for about 1.5 minutes, then transferred to a larger beaker containing 200 ml of cold corn oil and mixed with a Lightning Mixer at 800 rpm. The mixture was heated to 45° C. for about 45 minutes, then cooled down to room temperature. The resulting microspheres were repeatedly washed with petroleum ether to remove the oil and filtered. They were then dried overnight under vacuum at room temperature. The microspheres had diameters of between one and 20 microns.

EXAMPLE 2

Preparation of zein microspheres containing rhodamine B, a small organic molecule soluble in the zein solution.

Zein microspheres incorporating a fluorescent dye, rhodamine B, were prepared according to the procedure described in Example 1, except that 0,008 g rhodamine B (Sigma Chemical Co.) was used in lieu of insulin. Rhodamine B is soluble in the zein solution.

EXAMPLE 3

Preparation of zein microspheres containing soluble insulin.

Zein microspheres containing insulin were prepared according to the procedure outlined in Example 1, except that the final amount of insulin incorporated was either 17%, 30% or (w/w) and the insulin was dissolved in 90% ethanol-10% water, containing 5% zein (w/v) pH 2.5–3.0, (adjusted with 1N HCl). At this pH, insulin remains in solution with the zein. This mixture was then added to the corn oil mixture as described in example 1 to make insulin containing zein microspheres. SEM demonstrated that the microspheres have a dense structure.

EXAMPLE 4

Release kinetics in vitro of zein/insulin microspheres.

Microspheres with two different loadings of insulin, 4.8% and 9% (by weight) were produced as described in Example 1 using particulate insulin, and microspheres with three different loadings, 17%, 30%, and 42% (by weight), were produced with soluble insulin as described in example 3.

The release kinetics in vitro were determined by suspending 10 to 20 mg of the zein/insulin microspheres in 2.0 ml phosphate buffered saline (PBS) and incubating the suspension at 37° C. At various time intervals, 1 ml of PBS was decanted and replaced with 1 ml of fresh PBS. Insulin concentration was determined by reverse phase HPLC using a C18 Radial pak column (Waters, Milford, Mass.) with a water acetonitrile gradient.

The microspheres with 9% particulate insulin loading had an initial burst of release of 20% of the drug in a period of about ten hours, with linear release continuing over the next 40 hours. The microspheres with 4.8% particulate insulin loading had an approximate 5% initial release of the drug and linear release continuing over 50 hours.

The microspheres with the 17% soluble insulin had approximately 5% release initially with release rising to 7% after 24 hours with no further release for at least the next 90 hours. The microspheres with the 30% soluble insulin had approximately 8% release initially, and linear release over the next twenty hours to approximately 15%, with release continuing over at least the next seventy hours. The microspheres with the 42% soluble insulin had approximately 10% release initially, followed by linear release over the next 90 hours.

Samples collected at various time points were run on SDS-PAGE to check for degradation of the insulin. No degradation was observed.

EXAMPLE 5

Bioactivity of Zein/Insulin Microspheres in vivo.

A reproducible bioassay for insulin release is the measurement of blood glucose of diabetic rats following injection of the microspheres subcutaneously. Diabetes is induced in female Sprague-Dawley rats (Taconic Farms, N.Y.) by intravenously injecting 65 mg/kg streptozotocin (Upjohn Co., Kalamazoo, Mich.) in 0.1 M citrate buffer, pH 4.5.

12.0 mg of 17% (w/w) loading zein/insulin microspheres prepared as described in Example 3, in 1 ml normal saline, was administered to the rats. An equivalent dose of soluble (not encapsulated) insulin was injected into other rats as a control. The results of this experiment showed some differences in the length of biological activity between zein/ insulin microspheres and soluble insulin injected subcutaneously. The microspheres released insulin over a longer period of time and therefore resulted in a longer period of bioactivity than the soluble insulin.

EXAMPLE 6

Preparation of fatty acid modified zein.

Zein was modified with either hexanoic anhydride (C6), octanoic anhydride (C8), decanoic anhydride (C10) or lauric anhydride (C12). The zein and the specific anhydride were added to a medium consisting of 80% ethanol and 20% sodium borate (20 mM pH 9.0) and allowed to react with stirring at 37° C. for 2 hours with a five fold molar excess of anhydride. The pH was maintained by slow addition of sodium hydroxide during the time course of the reaction. After two hours, the solutions were acidified to pH 3.0 by addition of 37% HCl, and then extracted five times with several volumes of petroleum either to remove the free fatty acids. The material was dialyzed overnight against 2×15 L of distilled water, frozen at −80° C. and lyophilized.

EXAMPLE 7

Preparation of Deamidated Zein and Deamidated Zein Modified With Fatty Acid Microsphere Solution.

Deamidated zein was prepared as follows: a mixture of 5% (w/v) zein (Freeman Ind., Inc.) in 70% aqueous ethanol was titrated to pH 1.0 with 37% HCl (final HCl concentration approximately 0.12N) and incubated at 37° C. for 96 hours. The reaction was monitored with an ammonia electrode and the degree of deamidation determined. After 96 hours the reaction mixture was neutralized with 1M ammonium carbonate to terminate deamidation. The deamidated zein was recovered by dialysis against distilled water in 6000 molecular weight cutoff dialysis tubing (Spectrum). The deamidated zein precipitated during dialysis. The material was frozen at −80° C. and lyophilized in a shelf lyophilizer (The Virtis, Co., Gardiner, N.Y.)

Deamidated zein was modified with either hexanoic anhydride (C6), octanoic anhydride (C8), decanoic anhydride (C10) or lauric anhydride (C12). The deamidated zein and the specific anhydride were added to a medium consisting of 80% ethanol and 20% sodium borate (20 mM, pH 9.0) and allowed to react with stirring at 37° C. for 2 hours with a five fold molar excess of anhydride. The pH was maintained by slow addition of sodium hydroxide during the time course of the reaction. After two hours, the solutions were acidified to pH 3.0 by addition of 37% HCl, and then extracted five times with several volumes of petroleum ether to remove the free fatty acids. The material was dialyzed overnight against 2×15 L of distilled water, frozen at −80° C. and lyophilized.

EXAMPLE 8

In vitro Release Kinetics of Insulin from Zein and Fatty Acid Modified Zein Microspheres and Deamidated Zein and Deamidated Zein Modified With Fatty Acid Microspheres.

Zein, fatty acid modified zein, deamidated zein and fatty acid modified deamidated zein microspheres containing insulin were prepared according to the procedure outlined in Example 3. The amount of insulin incorporated was 17% (w/w).

The in vitro release kinetics of insulin from zein-C6, zein-C8, zein-C10 and zein-C12 microspheres were determined. The release kinetics were determined as in Example 5 and are shown in FIG. 1A.

Figure 1B:
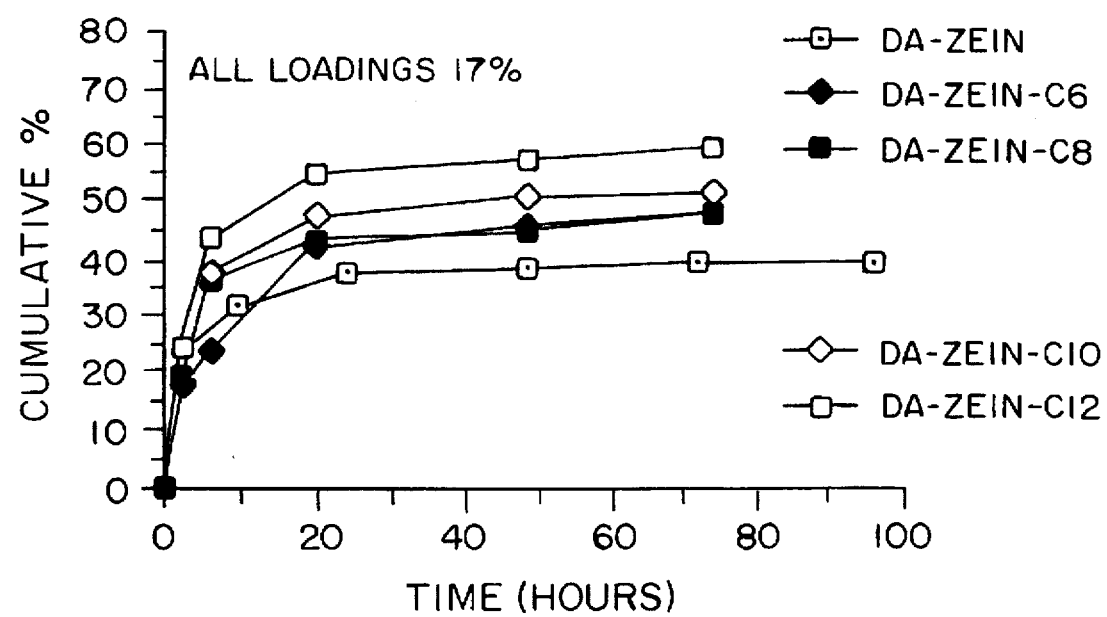
FIG. 1B is a plot of the % cumulative release of insulin into PBS from insulin containing microspheres prepared from deamidated zein and deamidated zein modified with hexanoic anhydride (C6), octanoic anhydride (C8), decanoic anhydride (C10) and lauric anhydride (C12) all having a 17% (w/w) loading of insulin versus time in hours.

The in vitro release kinetics of insulin from deamidated zein, deamidated zein-C6, deamidated zein-C8, deamidated zein-C10 and deamidated zein-C12 were determined. The release kinetics were monitored as in Example 5 and are shown in FIG. 1B.

EXAMPLE 9

In vivo activity of Zein-C6 and Deamidated Zein Insulin Microspheres.

The insulin containing microspheres formed from zein-C6 and deamidated zein prepared in examples 7 and 8 were tested for bioactivity as described in Example 5. Blood glucose levels of rats injected subcutaneously indicated that release from the microspheres occurs over an extended period of time and reduces the blood glucose levels.

EXAMPLE 10

Tracking of Zein and PLA Microspheres in the GI Tract.

Zein microspheres were incorporated with the fluorescent dye rhodamine B as described in Example 2. The zein/rhodamine microspheres were compared to PLA/rhodamine B microspheres prepared according to the following procedure: 1 g of PLA was dissolved in 10 ml of methylene chloride and 0.02 g rhodamine B was added. This solution was dispersed in an aqueous solution containing 1% (by weight) polyvinyl alcohol (DuPont, Wilmington, Del.), and the mixture was stirred overnight with a high shear mixer until all of the methylene chloride was evaporated, and microspheres formed. The microspheres were washed with water, filtered and dried in an oven. The fluorescent dye rhodamine B was used to permit tracking of the orally delivered microspheres in vivo.

Sprague-Dawley CD rats (Taconic Farms, N.Y.), weighing 175–225 g, were lightly anesthetized with methoxyflurane (Metafane, Pitman-Moore Inc., Washington Crossing, N.J.) and fed by gavage tube (20 in., 6 fr) with either 40–50 mg PLA/rhodamine microspheres or 20 mg Zein/rhodamine microspheres suspended in 1 ml isotonic saline. Rats were predosed with 60 mg of ranitidine by (p.o. Zantac™, Glaxo, Inc.) in 1 ml normal saline 3 hours prior to being fed the microspheres. Microsphere suspensions were sonicated for 2 minutes prior to feeding. Blood samples were taken via the tail vein at 30 minutes, 1 and 2 hours after introduction of the microspheres and collected in EDTA Microtainer tubes (Becton Dickinson, Paramus, N.J.).

Animals were anesthetized prior to each bleeding. Following the 2 hour blood sample, with the animal maintained under anesthesia, the abdomen was opened and the small intestines isolated. Rats were then sacrificed with 0.3 ml of sodium pentobarbital (Uthol, The Butler Company, Columbus, Ohio, 500 gr/ml). Peyer's patches, obtained from regions throughout the small intestinal tract, were excised and rapidly frozen in O.C.T. embedding media (Miles Inc., Elkhart Ind.) with an isopentane/dry ice slush.

Samples were stored in a -80° C. freezer until sectioned. Eight micron frozen sections were cut on a cryostat/microtome (Reichert Histostat, Cambridge Instruments co., N.Y.) and observed with an Olympus (Lake Success, N.Y.) BH2 microscope equipped for epi-illumination fluorescent microscopy with a 100 W high pressure mercury lamp and the appropriate filters for visualization of rhodamine. Blood samples were placed on acid washed microscope slides and similarly observed.

Zein/rhodamine and the PLA/rhodamine microspheres could be found both within the systemic circulation and within the intestinal wall one hour after oral administration. Microspheres localized within the intestinal wall were seen both in villi as well as in Peyer's patches. Samples of the spleen also contained PLA/rhodamine and zein/rhodamine microspheres.

EXAMPLE 11

Injection of Zein/Insulin Microspheres into an Isolated Ileal Loop.

An isolated ileal loop model was utilized to test the bioactivity of zein/insulin microspheres. Rats were anesthetized by methoxyflurane inhalation. The abdomen of the animal was shaved and scrubbed with betadine. The abdomen was opened with a midline incision and the intestines exposed. An approximately 10 cm length of the ileum was exposed. This segment was ligated distally with 3-0 silk suture. A small cut was made at the proximal end of the segment with microsurgical scissors. A suspension of 150 mg of zein/insulin (17% loading), made as described in Example 3, in PBS containing 0.01% Tween 80 and one microgram aprotinin was injected into the ileal segment using a 1 cc syringe attached to a 19 g. two inch plastic cannula. The cannula was inserted through the incision in the intestinal wall, and secured by a 3-0 silk suture tie around the intestine and the cannula. The microspheres were injected into the segment, the cannula was withdrawn from the incision, and the proximal suture tied off. The intestinal segment was replaced into the abdominal cavity, and the abdomen was closed with 4-0 Vicryl coated suture attached to a FS-2 cutting needle. The animals were maintained under anesthesia and kept on a heating pad for the duration of the 4 to 6 hour experiment.

Within four hours, blood glucose levels had fallen to about 25% of initial values, indicating release from the microspheres. Injection of unincorporated insulin into an ileal loop produced no significant drop in blood glucose levels.

EXAMPLE 12

Oral Administration of Zein Microspheres Containing Insulin to Diabetic Rats.

Figure 2:
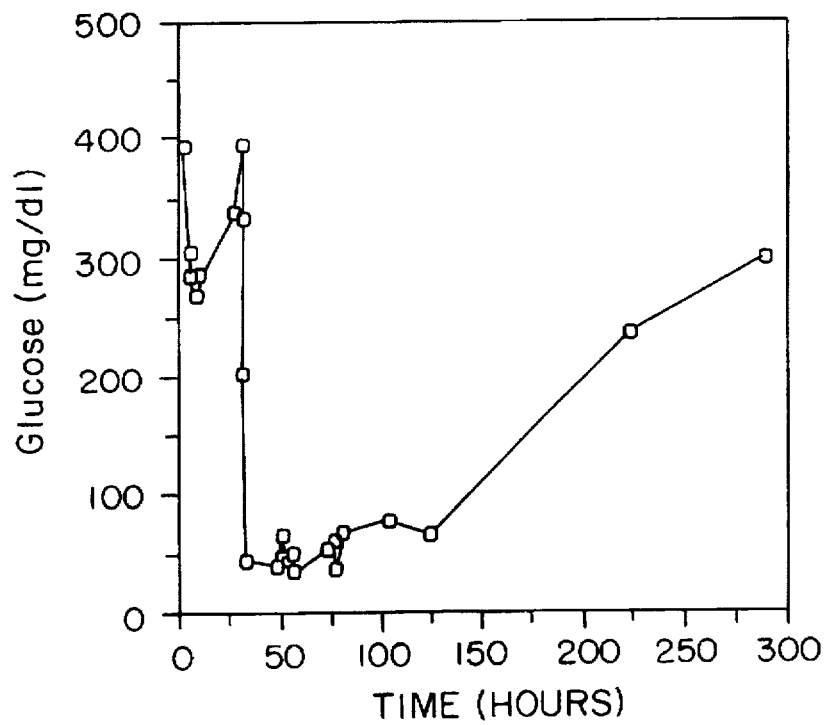
FIG. 2 is a graph of the blood glucose (mg/dl) in diabetic rats orally administered zein/insulin microparticles over time (hours).

Diabetes was induced in a Sprague Dawley rat (Taconics, Germantown, N.Y.) by injecting intravenously streptozotocin (Upjohn Co., Kalamazoo, Mich.) at a dose of 65 mg/kg in 0.1M citrate buffer pH 4.5. Two weeks after induction the rat was fed by gayage the microspheres containing 17% w/w insulin as prepared in example 3 (120 mg in 2 ml of normal saline each morning for three days). Each day the animal was lightly anesthetized with Metofane (Pitman Moore Inc., Washington Crossing, N.J.) and 150 mg of Zantac™ (Glexco Inc.) in 2 ml of normal saline was fed to the animal via a 5 french gavage tube. Three hours after the Zantac™ administration, the animal was lightly anesthetized with Metofane and the microspheres were given to the animal using a 5 fr gavage tube. The blood glucose levels were monitored by sampling from the animal's tail vein and using a Glucometer II (Boerhinger Ingelheim) glucose meter. The animal's blood glucose profile is shown in FIG. 2.

EXAMPLE 13

Enteral Administration of Zein Microspheres Containing Insulin to Diabetic Rats.

Figure 3:
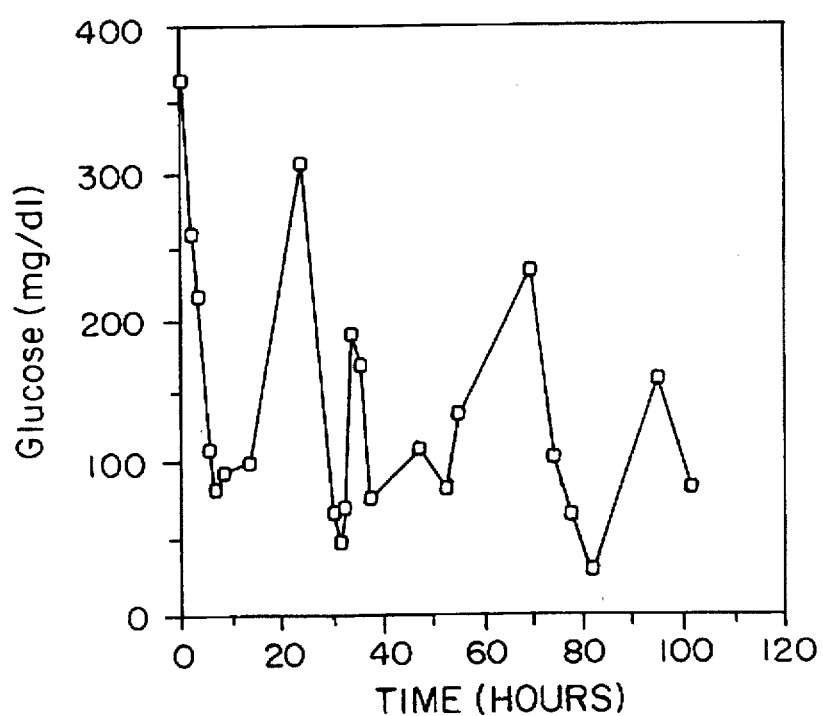
FIG. 3 is a graph of the blood glucose (mg/dl) in diabetic rats enterally administered zein/insulin microspheres over time (hours).

Diabetes was induced in a Sprague Dawley rat (Taconics, Germantown, N.Y.) by injecting intravenously streptozotocin (Upjohn Co., Kalamazoo, Mich.) at a dose of 65 mg/kg in 0.1M citrate buffer pH 4.5. A duodenal catheter was surgically implanted two weeks after the induction of diabetes. The catheter was made of PE 90 tubing and was secured in the duodenum using dexon and Vetbond tissue adhesive (3M). Post operatively, the animal was given a one week course of ampicillin (4 mg subcutaneously twice daily). The microspheres containing 17% insulin (w/w) of example 3 (160 mg) were resuspended in 1.0 ml of PBS with 0.3% Tween 80/0.2% Span 80 and infused directly into the small intestine via the catheter using a 1 cc syringe. The blood glucose levels were monitored by sampling from the animal's tail vein and using a Glucometer II (Boerhinger Ingelheim) glucose meter. The animal's blood glucose profile is shown in FIG. 3.

EXAMPLE 14

Incorporation of Vasopressin into zein/lysine microspheres.

The bioactivity of zein/lysine vasopressin (LVP) microspheres, prepared with 1.7 mg of 51.1% lypressin (Sandoz Research, East Hanover, N.J.) and 240 mg zein (0.36% loading) as described in example 3, was tested in Brattleboro strain rats homozygous for diabetes insipidus (DI rats). These rats lack detectable vasopressin and drink and excrete large quantities of water as compared to vasopressin-replete Brattleboro heterozygous and Long-Evans strain controls. DI rats (Harlan Sprague Dawley, Indianapolis, Ind.), maintained in metabolic cages, were first monitored for several weeks to determine baseline water intake and excretion values. Once baseline water balance values had been measured, the zein/LVP microspheres were tested by both subcutaneous and intraperitoneal injection. Animals were injected with 1.5 and 4.5 mg of 0.5% LVP loaded microspheres (7.5 and 22.5 µg of incorporated LVP) suspended in phosphate buffered saline containing 0.35% Tween 80, 0.15% Span 80, and 0.1% CMC. Significant decreases in both water intake and urine output were observed at both dose levels and for both subcutaneous and intraperitoneal injections. For both subcutaneous and intraperitoneal injection, this effect lasted for about 8 hr with the 7.5 µg doses, and from 30 to 40 hr for the 22.5 µg doses. When similar amounts of unincorporated LVP were injected subcutaneously or intraperitoneally, the effect did not last longer than 8 hours.

These results demonstrate that the microspheres incorporating vasopressin provided sustained release of LVP in vivo.

Modifications and variations of the method for delivery of biologically active compounds will be obvious to those skilled in the art from the foregoing detailed description. Such modifications and variations are intended to come within the scope of the appended claims.

We claim:

1. A method for administering a biologically active compound comprising administering at a site the compound in a prolamine microsphere produced by
   a) contacting a protein solution, wherein the protein consists of prolamine, and contains biologically active compound to be incorporated, with an oil, which is of limited miscibility with the prolamine solvent and does not dissolve the prolamine, to form a prolamine-oil mixture having a ratio of 1:18.75, prolamine solvent:oil;
   b) agitating the prolamine-oil mixture to form a dispersion of the prolamine solution in the oil; and
   c) extracting the prolamine solvent into the oil to form stable prolamine microspheres having dispersed throughout the prolamine the biologically active compound,
   wherein all of the procedures are performed at a temperature which does not denature the prolamine and the resulting prolamine microsphere has a diameter between 50 nm and 100 microns and releases incorporated compound in a controlled manner in the absence of amide linkages or heat denaturation of the prolamine.

2. The method of claim 1 wherein the prolamine is selected from the group consisting of zein, gliadin, hordein and kafirin.

3. The method of claim 1 wherein the prolamine has been modified prior to formation of the microspheres.

4. The method of claim 3 wherein the prolamine is chemically modified.

5. The method of claim 4 wherein the prolamine is deamidated with acid.

6. The method of claim 4 wherein the prolamine is chemically modified by esterification with a fatty alcohol.

7. The method of claim 4 wherein the prolamine is chemically modified by acylation with a fatty anhydride.

8. The method of claim 4 wherein the prolamine is chemically modified by coupling amino acids, peptides or proteins to the prolamine.

9. The method of claim 3 wherein the prolamine is cleaved enzymatically into smaller molecular weight fragments.

10. The method of claim 1 further comprising adding a non-protein polymer to the prolamine microspheres.

11. The method of claim 10 wherein the non-protein polymer is selected from the group consisting of poly(lactic acid), poly(glycolic acid), polyanhydride, polyorthoesters, polyphosphazene, polyhydroxybutyrate, polycaprolactone, polyamides, blends and copolymers, and combinations thereof.

12. The method of claim 1 wherein the microspheres contain particles insoluble in the prolamine solution.

13. The method of claim 1 wherein the biologically active compound is selected from the group consisting of pharmaceuticals, pesticides, nutrients, imaging agents, bacteria and metal binding agents.

14. The method of claim 1 wherein the microsperes are aggregated into a form containing multiple microspheres.

15. The method of claim 14 wherein the microspheres contain a first biologically active compound and the aggregate contains a second biologically active compound.

16. The method of claim 1 wherein the microspheres are in a pharmaceutically acceptable carrier.

17. The method of claim 16 wherein the microspheres are administered topically in a suitable pharmaceutical carrier.

18. The method of claim 16 wherein the microspheres are administered parenterally.

19. The method of claim 16 wherein the microspheres are administered enterally.

20. The method of claim 1 wherein the biologically active compound is selected from the group consisting of pesticides, fertilizers, proteases, metal binding compounds, cellulases, lipases, and enzymes in degradation of plastics and polychlorinated biphenyls.

21. The method of claim 20 further comprising locating the microspheres at an appropriate site in the environment for subsequent release of the biologically active compound.

22. A method for adhering substances to tissue and enamel comprising administering the substances incorporated into prolamine microspheres produced by
   a) contacting a protein solution, wherein the protein consists of prolamine, and contains biologically active compound to be incorporated, with an oil, which is of limited miscibility with the prolamine solvent and does not dissolve the prolamine, to form a prolamine-oil mixture having a ratio of 1:18.75, prolamine solvent:oil;
   b) agitating the prolamine-oil mixture to form a dispersion of the prolamine solution in the oil; and
   c) extracting the prolamine solvent into the oil to form stable prolamine microspheres having dispersed throughout the prolamine the biologically active compound,
   wherein all of the procedures are performed at a temperature which does not denature the prolamine and the resulting prolamine microsphere has a diameter between 50 nm and 100 microns and releases incorporated compound in a controlled manner in the absence of amide linkages or heat denaturation of the prolamine.

23. The method of claim 22 wherein the substances are biologically active compounds in combination with zein.

* * * * *

UNITED STATES PATENT AND TRADEMARK OFFICE
CERTIFICATE OF CORRECTION

PATENT NO. : 5,679,377
DATED : October 21, 1997
INVENTOR(S) : Howard Bernstein, Eric Morrel, Edith Mathiowitz, Kirsten Schwaller and Thomas R. Beck It is certified that error appears in the above-identified patent and that said Letters Patent is hereby corrected as shown below:

In Column 17, line 18:     After the words "ratio of", delete "1:18.75" and insert therefor --1: $\geq$ 18.75--; and In Column 18, line 39:     After the words "ratio of", delete "1:18.75" and insert therefor --1: $\geq$ 18.75--.

Signed and Sealed this

Thirtieth Day of December, 1997

Attest:

BRUCE LEHMAN

*Attesting Officer*      *Commissioner of Patents and Trademarks*